United States Patent
Hoan et al.

(10) Patent No.: US 8,657,843 B2
(45) Date of Patent: Feb. 25, 2014

(54) SHIELD LOCKOUT FOR BLADED OBTURATOR AND TROCARS

(75) Inventors: Andrew N. Hoan, Irvine, CA (US); Noreen Jue, Aliso Viejo, CA (US); Luca Pesce, Lake Forest, CA (US); Russell E. Ahlberg, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1257 days.

(21) Appl. No.: 12/106,227

(22) Filed: Apr. 18, 2008

(65) Prior Publication Data

US 2008/0228214 A1 Sep. 18, 2008

Related U.S. Application Data

(63) Continuation-in-part of application No. 11/744,108, filed on May 3, 2007.

(60) Provisional application No. 60/746,313, filed on May 3, 2006, provisional application No. 60/912,679, filed on Apr. 18, 2007.

(51) Int. Cl.
*A61B 17/34* (2006.01)

(52) U.S. Cl.
USPC .......................................................... 606/185

(58) Field of Classification Search
USPC ...................... 606/167, 184, 185, 170, 172; 604/165.01, 164.08, 164.11, 164.12
See application file for complete search history.

(56) References Cited

U.S. PATENT DOCUMENTS

| | | | |
|---|---|---|---|
| 4,601,710 | A | 7/1986 | Moll |
| 4,654,030 | A | 3/1987 | Moll et al. |
| 4,931,042 | A | 6/1990 | Holmes et al. |
| 5,030,206 | A | 7/1991 | Lander |
| 5,114,407 | A | 5/1992 | Burbank |
| 5,224,952 | A | 7/1993 | Deniega et al. |
| 5,226,426 | A | 7/1993 | Yoon |
| 5,246,425 | A | 9/1993 | Hunsberger et al. |
| 5,275,583 | A | 1/1994 | Crainich |
| 5,290,243 | A | 3/1994 | Chodorow et al. |
| 5,312,354 | A | 5/1994 | Allen et al. |
| 5,314,417 | A | 5/1994 | Stephens et al. |
| 5,318,580 | A | 6/1994 | Gresl, Jr. |

(Continued)

FOREIGN PATENT DOCUMENTS

WO   WO 94/09712   5/1994

OTHER PUBLICATIONS

The International Bureau of WIPO, International Preliminary Report on Patentability, for International Application No. PCT/US2008/060928, dated Oct. 20, 2009, entitled Shield Lockout for Bladed Obturator and Trocars.

(Continued)

*Primary Examiner* — Thomas McEvoy
(74) *Attorney, Agent, or Firm* — John F. Heal; David G. Majdali

(57) ABSTRACT

A shielded bladed obturator is provided with a shield lockout that prevents retraction of a shield to expose a blade for cutting. The shield lockout in one aspect has a rotational switch interacting with a longitudinal extending shield to lock and unlock the shield. A blade exposure and coverage system is also provided.

14 Claims, 15 Drawing Sheets

(56) References Cited

U.S. PATENT DOCUMENTS

| | | | |
|---|---|---|---|
| 5,330,432 A | 7/1994 | Yoon | |
| 5,338,305 A | 8/1994 | Plyley et al. | |
| 5,342,382 A | 8/1994 | Brinkerhoff et al. | |
| 5,350,393 A | 9/1994 | Yoon | |
| 5,356,421 A | 10/1994 | Castro | |
| 5,360,405 A | 11/1994 | Yoon | |
| 5,364,365 A | 11/1994 | Wortrich | |
| 5,364,372 A | 11/1994 | Danks et al. | |
| 5,366,445 A | 11/1994 | Haber et al. | |
| 5,372,588 A | 12/1994 | Farley et al. | |
| 5,387,197 A | 2/1995 | Smith et al. | |
| 5,399,167 A | 3/1995 | Deniega | |
| 5,411,515 A | 5/1995 | Haber et al. | |
| 5,417,705 A | 5/1995 | Haber et al. | |
| 5,462,532 A | 10/1995 | Gresl | |
| 5,474,539 A | 12/1995 | Costa et al. | |
| 5,486,190 A | 1/1996 | Green | |
| 5,527,335 A | 6/1996 | Bolduc et al. | |
| 5,536,256 A | 7/1996 | Yoon | |
| 5,569,289 A | 10/1996 | Yoon | |
| 5,584,848 A | 12/1996 | Yoon | |
| 5,599,347 A * | 2/1997 | Hart et al. | 606/42 |
| 5,609,604 A | 3/1997 | Schwemberger et al. | |
| 5,618,297 A | 4/1997 | Hart et al. | |
| 5,620,456 A | 4/1997 | Sauer et al. | |
| 5,624,459 A | 4/1997 | Kortenbach et al. | |
| 5,634,934 A | 6/1997 | Yoon | |
| 5,645,076 A | 7/1997 | Yoon | |
| 5,645,556 A | 7/1997 | Yoon | |
| 5,645,557 A | 7/1997 | Yoon | |
| 5,665,072 A | 9/1997 | Yoon | |
| 5,665,102 A | 9/1997 | Yoon | |
| 5,674,237 A | 10/1997 | Ott | |
| 5,676,156 A | 10/1997 | Yoon | |
| 5,676,681 A | 10/1997 | Yoon | |
| 5,690,663 A | 11/1997 | Stephens | |
| 5,697,947 A | 12/1997 | Wolf et al. | |
| 5,776,112 A | 7/1998 | Stephens et al. | |
| 5,779,680 A | 7/1998 | Yoon | |
| 5,807,402 A | 9/1998 | Yoon | |
| 5,851,216 A | 12/1998 | Allen | |
| 5,868,773 A | 2/1999 | Danks et al. | |
| 5,904,699 A | 5/1999 | Schwemberger et al. | |
| 5,916,232 A * | 6/1999 | Hart | 606/185 |
| 5,980,493 A | 11/1999 | Smith et al. | |
| 5,984,941 A | 11/1999 | Wilson et al. | |
| 5,997,510 A | 12/1999 | Schwemberger | |
| 6,017,356 A | 1/2000 | Frederick et al. | |
| 6,063,099 A | 5/2000 | Danks et al. | |
| 6,099,544 A | 8/2000 | Wolf et al. | |
| 6,238,407 B1 | 5/2001 | Wolf et al. | |
| 6,319,266 B1 | 11/2001 | Stellon et al. | |
| 6,340,358 B1 | 1/2002 | Bohannon et al. | |
| 6,402,770 B1 | 6/2002 | Jessen | |
| 6,716,201 B2 | 4/2004 | Blanco | |
| 6,837,874 B1 | 1/2005 | Popov | |
| 6,939,351 B2 | 9/2005 | Eckman | |
| 6,960,164 B2 | 11/2005 | O'Heeron | |
| 2001/0029387 A1 | 10/2001 | Wolf et al. | |
| 2002/0026207 A1 | 2/2002 | Stellon et al. | |
| 2002/0161387 A1 | 10/2002 | Blanco | |
| 2003/0045834 A1 | 3/2003 | Wing | |
| 2003/0060770 A1 | 3/2003 | Wing et al. | |
| 2004/0049173 A1 | 3/2004 | White et al. | |
| 2004/0116864 A1 | 6/2004 | Boudreaux | |
| 2004/0147949 A1* | 7/2004 | Stellon et al. | 606/185 |
| 2004/0230155 A1 | 11/2004 | Blanco et al. | |
| 2005/0209623 A1 | 9/2005 | Patton | |
| 2006/0052811 A1 | 3/2006 | Blanco | |

OTHER PUBLICATIONS

International Searching Authority (US), The International Search Report and The Written Opinion of the International Searching Authority for International Application No. PCT/US/060928 mailed Sep. 2, 2008.

* cited by examiner

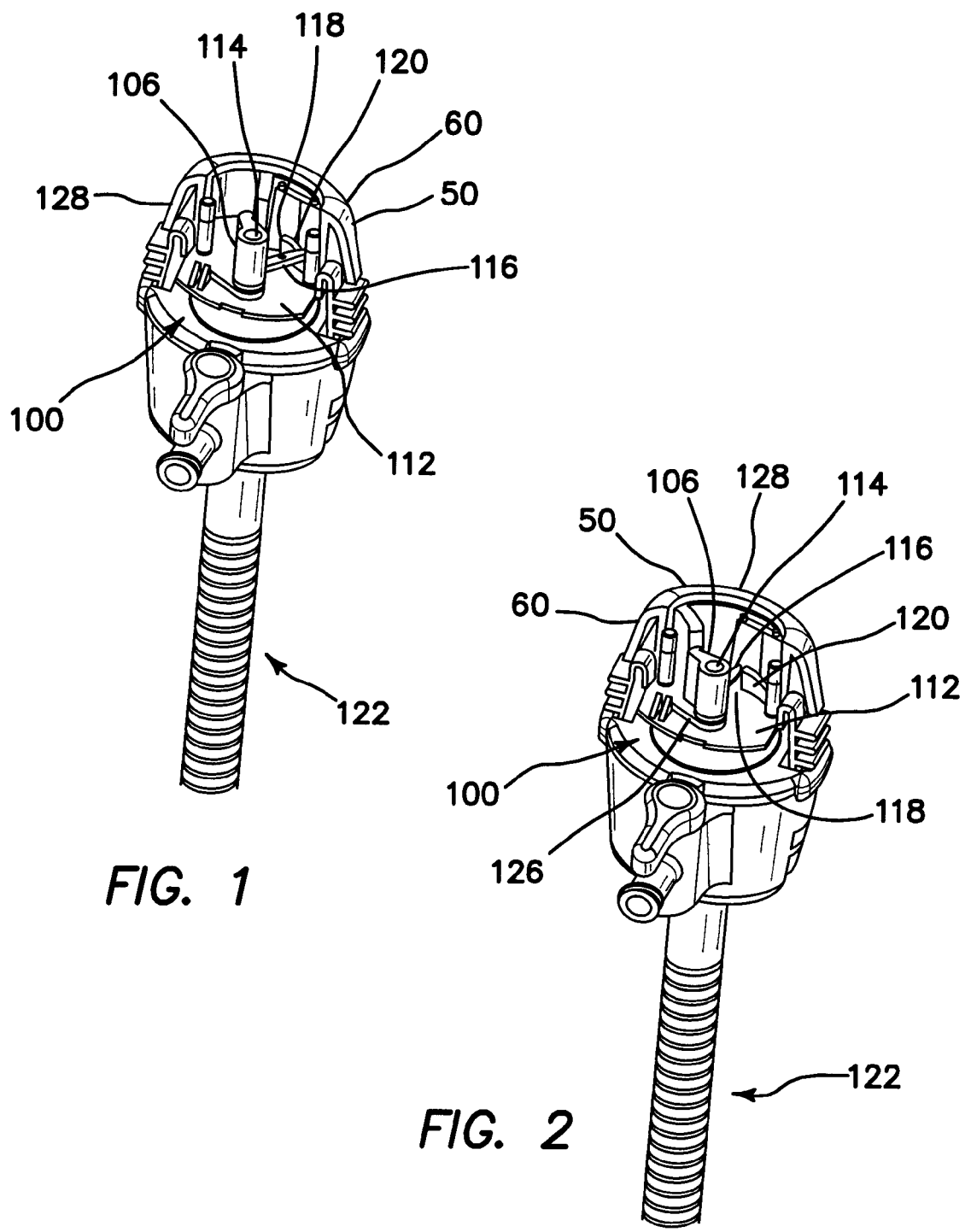

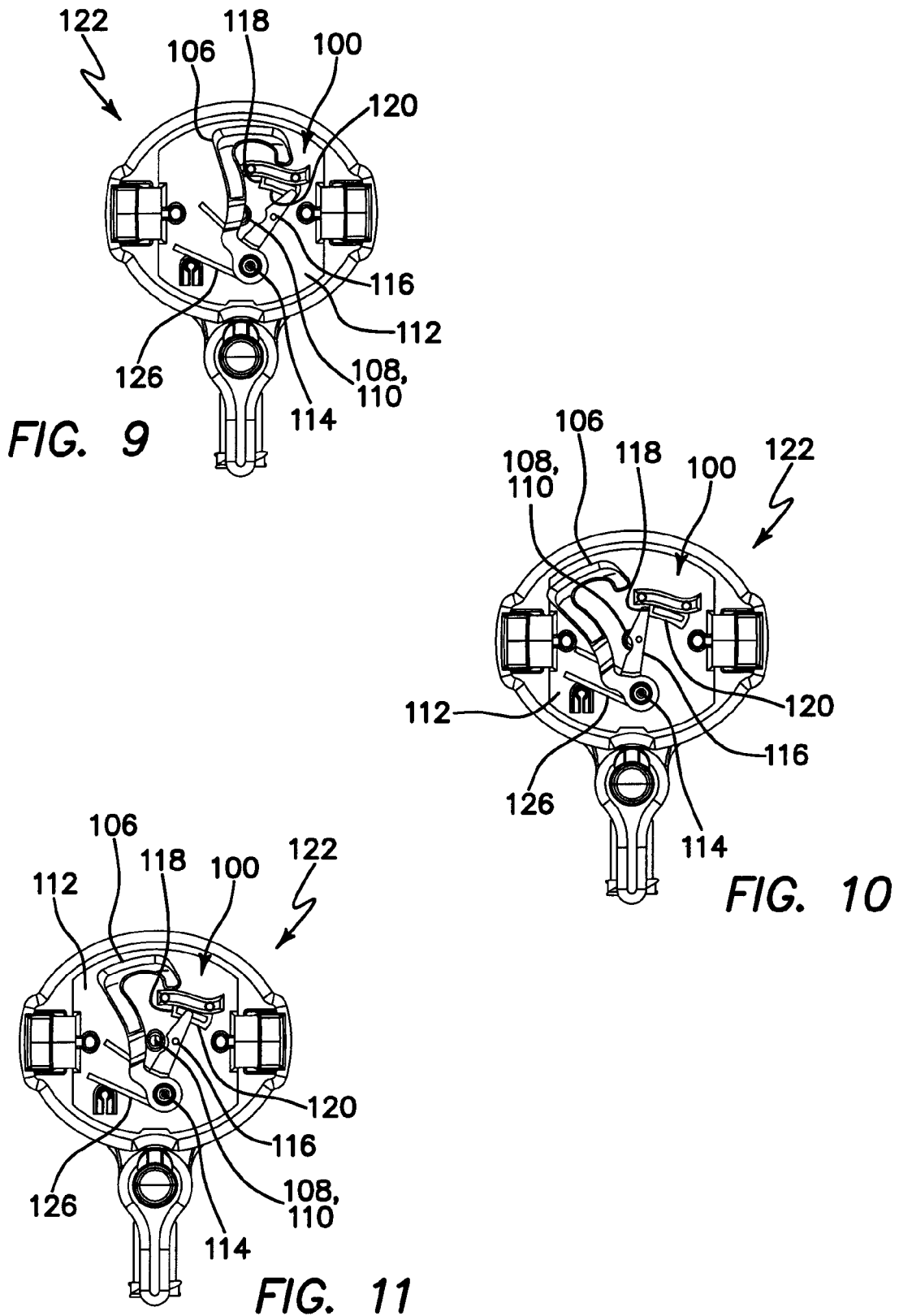

SHIELD LOCKOUT FOR BLADED OBTURATOR AND TROCARS

CROSS-REFERENCE TO RELATED APPLICATIONS

This application is a continuation-in-part of U.S. patent application Ser. No. 11/744,108, filed May 3, 2007, that claims the benefit of U.S. Provisional Application No. 60/746,313, filed May 3, 2006, the disclosures of which are hereby incorporated by reference as if set forth in full herein. This application also claims the benefit of U.S. Provisional Application No. 60/912,679, filed Apr. 18, 2007, the disclosure of which is hereby incorporated by reference as if set forth in full herein.

BACKGROUND

This invention relates generally to trocars or access ports used in endoscopic or laparoscopic surgeries and more particularly, to flat blade shielded obturators.

A surgical access port or trocar generally has a cannula and a valve housing coupled to one end of the cannula and an obturator inserted into the cannula has a shaft with a sharp blade or tip at one end of the shaft. In operation, the trocar cannula extends across a body wall, e.g., the abdominal wall, providing access into a body cavity, such as the abdominal cavity. The obturator facilitates the placement of the trocar by puncturing and/or penetrating the tissue forming the body wall.

In one example, the obturator is inserted through the cannula and its sharp bladed tip extends beyond one end of the cannula. The sharp bladed tip of the obturator cuts tissue as the trocar and obturator are moved through the body wall. Once the trocar and obturator are operatively positioned, the obturator can be removed from the trocar body leaving the cannula to provide working-channel access into the body cavity.

With the body wall penetrated, the sharp bladed tip can be covered or protected. For example, a spring-loaded tubular safety shield which surrounds the shaft of the obturator may move forward to cover the tip of the obturator once resistance to the movement of the safety shield, e.g., from the body wall, is removed. As such, the cutting stops once the body wall has been penetrated. However, a relatively large force may be required to cause the tip of an obturator to penetrate the body wall. Once the tip penetrates the body wall, resistance to penetration is removed and the tip of the obturator is suddenly free to reach into the body cavity and cause additional cutting. Failure to stop this cutting action can result in complications. Obturators having spring-loaded tubular safety shields may require larger incisions and may require considerable time to move the shield to cover the tip, the shield possessing a relatively large mass.

SUMMARY

Generally, a flat blade shielded obturator is provided. A shield lockout is provided that facilitates assembly, enhances reliability and reduces complex mechanisms. In one aspect, an obturator comprises a handle having a switch movable from a first, locked position to a second, unlocked position. The switch has a first section and a second section. Connected to the handle, the obturator also has a shaft having a movable portion and a fixed portion with a blade connected to the fixed portion of the shaft. The shaft has a longitudinal axis. The switch in the first position has the first section of the switch obstructing the movable portion of the shaft to prevent movement of the movable portion of the shaft along the longitudinal axis. In the second position, the switch has the second section of the switch obstructing the movable portion of the shaft and allowing movement of the movable portion of the shaft along the longitudinal axis.

In one aspect, the first section of the switch is a first arm coupled to a user accessible tab and the second section of the switch is a second arm smaller than the first arm. The second arm is deflectable in a direction parallel to the longitudinal axis of the shaft. The first arm is not deflectable. The user accessible tab and first section may be movable to the second position with the user accessible tab returning to the first position while the first section remains in the second position. The obturator may have a wall within the handle that is exposed when the switch is moved to the second position. The second section is movable along a direction parallel to the longitudinal axis. The first section is not movable along a direction parallel to the longitudinal axis. The first and second sections are rotatable about a longitudinal axis offset from and parallel to the longitudinal axis of the shaft. The obturator further comprises a ramp obstructing movement of the switch in the second position and allowing movement of the switch in the first position. The ramp has a first, low profile end and a second, high profile end. The second section of the switch is adapted to ride along the ramp while deflecting and to snap into a locked position along a back wall of the ramp, juxtaposed to the high profile end of the ramp, thereby locking the switch into the second position. The second section may be a spring. The second section may be more resilient than the first section.

Many of the attendant features of the present invention will be more readily appreciated as the same becomes better understood by reference to the foregoing and following description and considered in connection with the accompanying drawings in which like reference symbols designate like parts throughout.

BRIEF DESCRIPTION OF DRAWINGS

FIG. 1 is a perspective view of a trocar system in accordance with various aspects of the present invention;

FIG. 2 is a perspective view of a trocar system in accordance with various aspects of the present invention;

FIG. 9 is a top view of an obturator in accordance with various aspects of the present invention;

FIG. 10 is a top view of an obturator in accordance with various aspects of the present invention;

FIG. 11 is a top view of an obturator in accordance with various aspects of the present invention;

DETAILED DESCRIPTION

Figure 3:
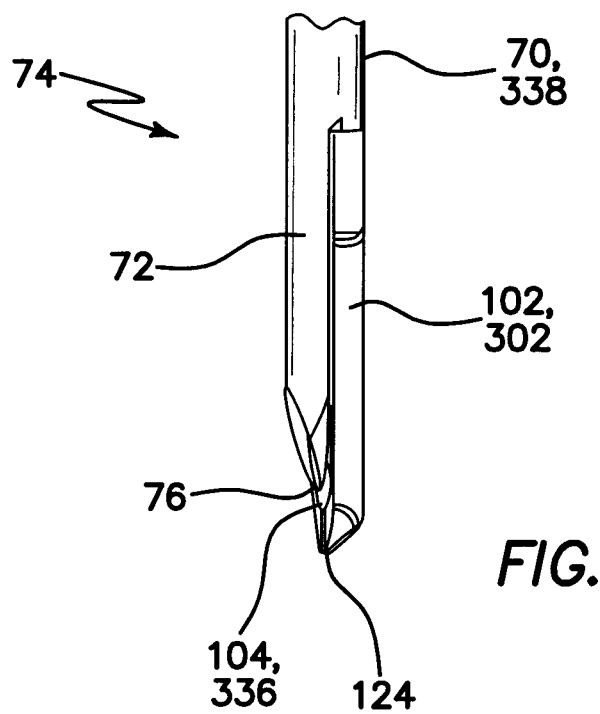
FIG. 3 is a side view of a distal portion of an obturator of a trocar system in accordance with various aspects of the present invention.
Figure 4:
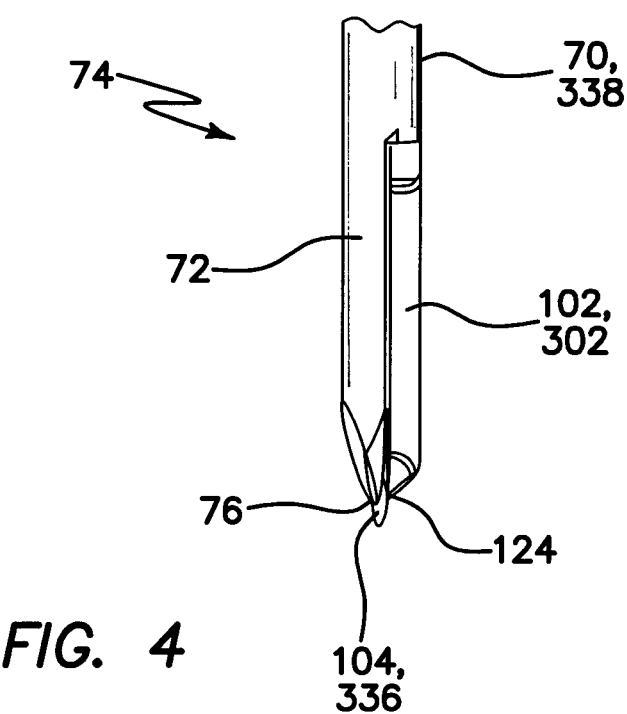
FIG. 4 is a side view of a distal portion of an obturator of a trocar system in accordance with various aspects of the present invention.
Figure 5:
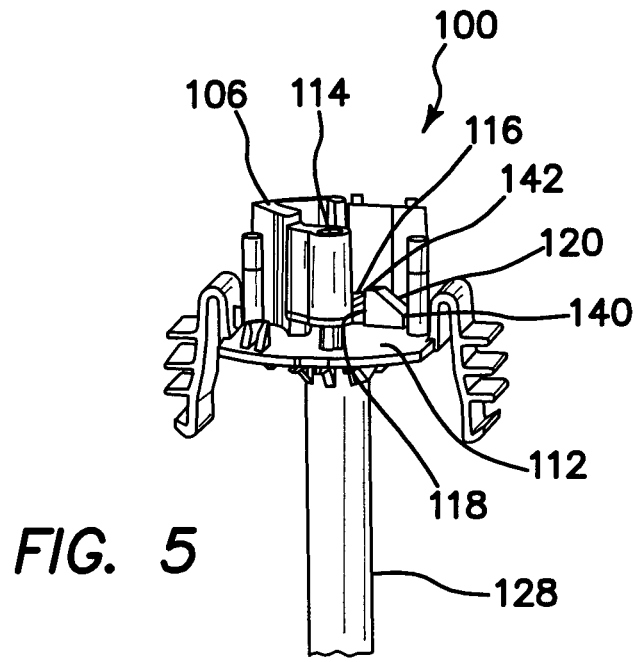
FIG. 5 is a perspective view of a proximal portion of an obturator in accordance with various aspects of the present invention.
Figure 6:
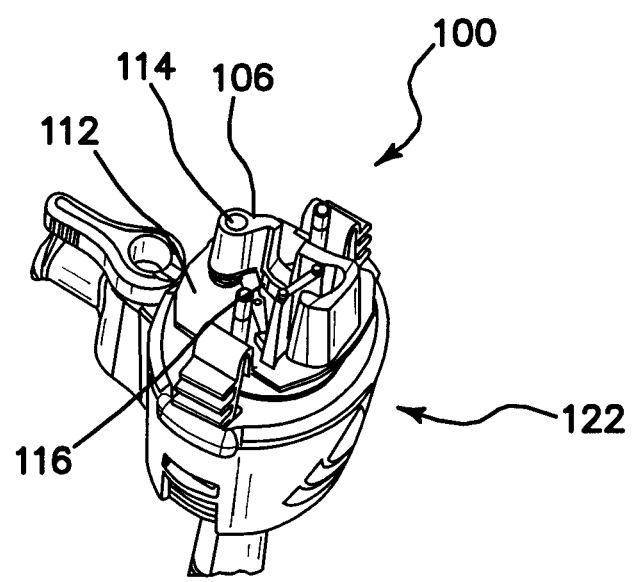
FIG. 6 is a perspective view of a proximal portion of an obturator in accordance with various aspects of the present invention.
Figure 7:
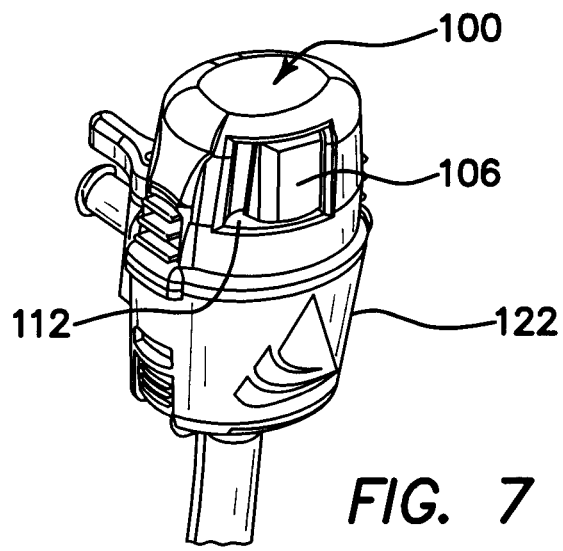
FIG. 7 is a perspective view of a proximal portion of an obturator in accordance with various aspects of the present invention.
Figure 8:
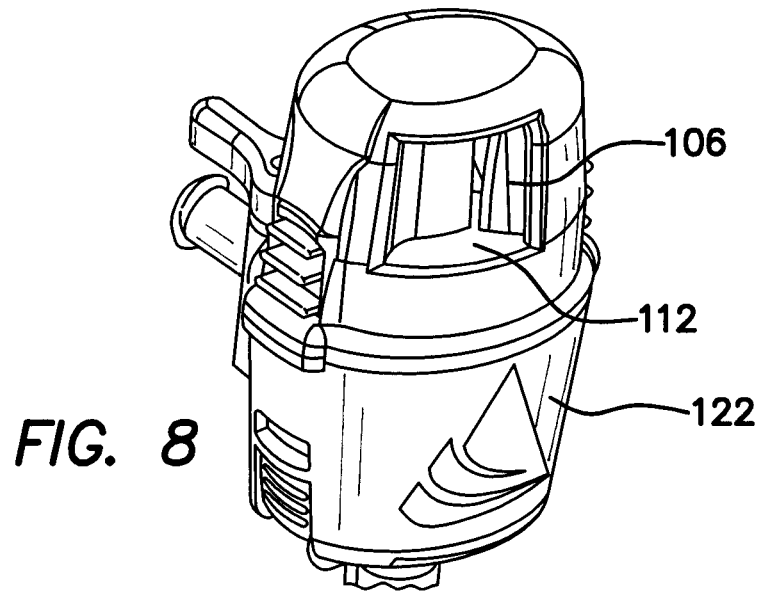
FIG. 8 is a perspective view of a proximal portion of an obturator in accordance with various aspects of the present invention.
Figure 12:
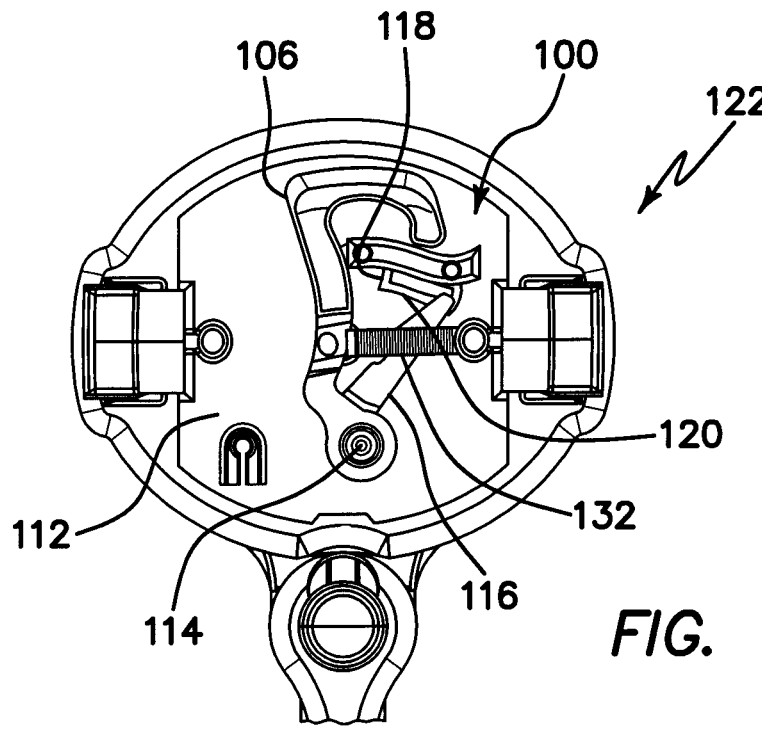
FIG. 12 is a top view of an obturator in accordance with various aspects of the present invention.
Figure 13:
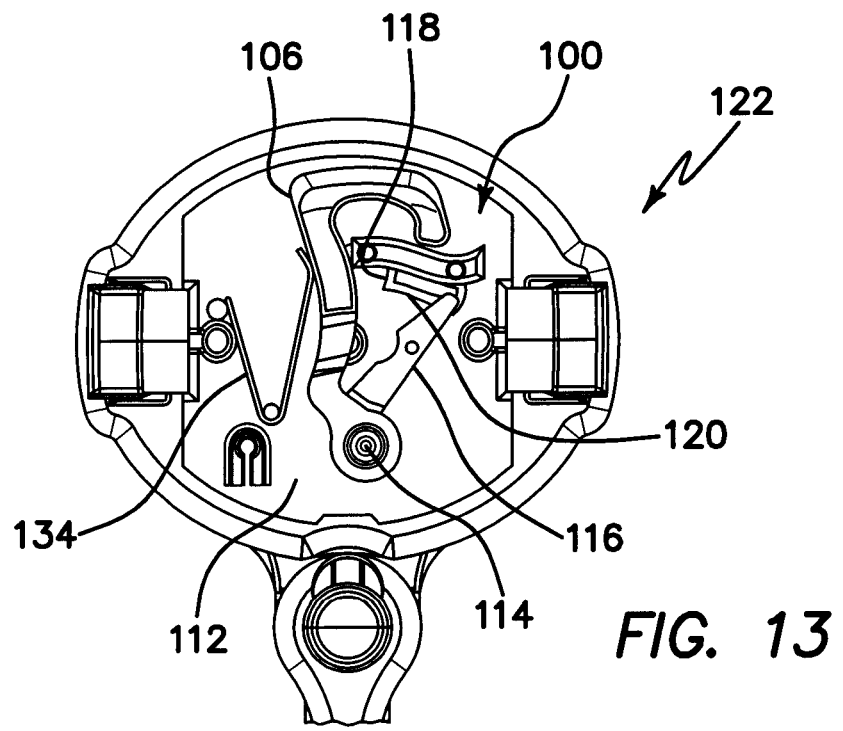
FIG. 13 is a top view of an obturator in accordance with various aspects of the present invention.

In FIGS. 1-13, an obturator 50 has a handle 60 and a shaft 70. The handle 60 has a switch 100 movable from a first, locked position to a second, unlocked position. The switch 100 has a first section, or arm 106, and a second section, or arm 116, each extending from a pivot post 114. The shaft 70 is connected to the handle 60 and has a longitudinal axis. The shaft 70 has a movable portion, or shield 102, and a fixed portion 72. A blade 104 is connected to a distal portion 74 of the fixed portion 72 of the shaft 70 and extends distally beyond a distal end 76 of the fixed portion of the shaft. The movable portion 102 of the shaft 70 functions as a blade shield and is movable between a first, distal position, wherein it inhibits contact with the blade 104 to prevent cutting, to a second, proximal position, wherein the blade is exposed for cutting. With the switch 100 in the first, locked position, the first section 106 of the switch obstructs the shield portion 102 of the shaft 70 to prevent movement of the shield along the longitudinal axis. With the switch 100 in the second, unlocked position, the second section 116 of the switch obstructs the shield 102, but allows the shield to move proximally along the longitudinal axis, thereby exposing the blade 104.

As indicated above, the switch 100 is manipulated by a user, e.g., a surgeon, to manually unlock the movable portion, or shield 102 of the shaft 70, allowing the blade shield to travel proximally, thereby exposing the blade 104 for cutting. The movable portion 102 of the shaft 70 has a shield shaft 110 that is adapted to move proximally into the handle 60 of the obturator 50. When the switch 100 is in the locked position (FIG. 1), it overlaps a proximal end 108 of a shield shaft 110 which extends through a center of a base plate 112.

The switch 106 is rotatable about a pivot post 114 mounted on the base plate 112 offset from the longitudinal axis of the shaft. As the switch 106 rotates to unlock the shield 102, the proximal end 108 of the shield shaft 110 is unobstructed and allowed to retract proximally into the handle 100 (FIG. 2). The switch 100 is held in the unlocked position by the second arm 116 of the switch. The second arm 116, which is deflectable in a direction parallel to the longitudinal axis of the shaft 70, locks on the back side 118 of a ramp 120 extending from the base plate 112. More particularly, the ramp 120 has a first, low profile end 140 and a second, high profile end 142. The second arm 116 of the switch 100 is adapted to ride along the ramp 120 while deflecting and to snap into a locked position along the back side 118 of the ramp, which is juxtaposed to the high profile end of the ramp, thereby locking the switch into the second position. The ramp 120 obstructs movement of the switch 100 in the second position and allows movement of the switch in the second position. While the second arm 116 is deflectable, the first arm 106 is not deflectable.

Figure 22:
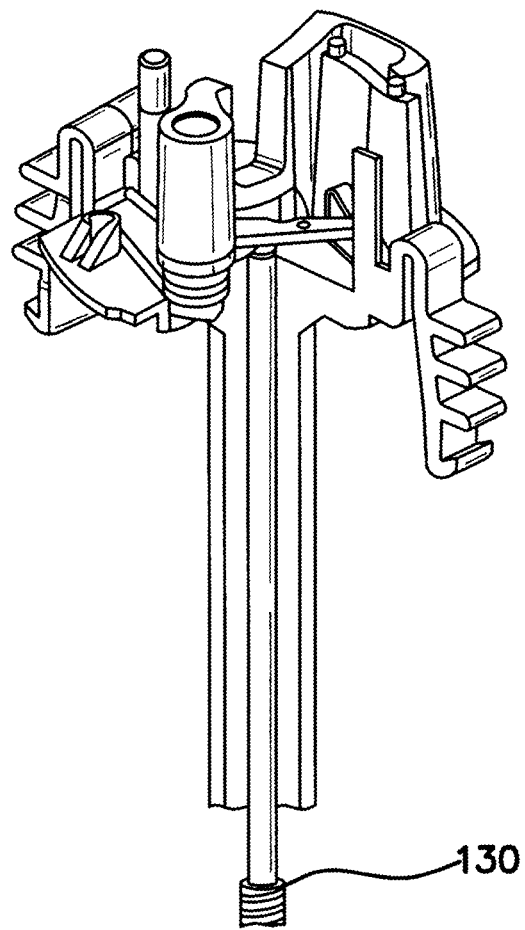
FIG. 22 is a perspective view of an obturator in accordance with various aspects of the present invention.

When the trocar assembly 122 is inserted through an abdominal wall, the shield 102 retracts due to insertion pressure on the distal tip 124 of the shield. The proximal end 108 of the shield shaft 110 makes contact with the second arm 116 which is locked on the back wall 118 of the base plate ramp 120. As contact is made, the shield shaft 110 lifts the second arm 116 up over the ramp 120 releasing the switch 100. A torsion spring 126 connected between the base plate 112 and switch 100 forces the switch back to its original position. However, the switch 100 stops short as the first arm 106 of the switch is biased against the proximal end 108 of the shield shaft 110 while the shield 102 is retracted during insertion. As the obturator 128 clears the inside edge of the abdominal wall, the shield 102, which is compressing a compression spring 130 (FIG. 22) between itself and the base plate 112, is allowed to extend back forward to a shielded position, thereby preventing the blade 104 from performing additional cutting. As the proximal end 108 of the shield shaft 110 moves distally beyond contact with the second arm 116 of the switch, the shield shaft releases or no longer obstructs the spring loaded switch 100, thereby allowing the switch to return back to its original, locked position (FIG. 1).

Figure 14A:
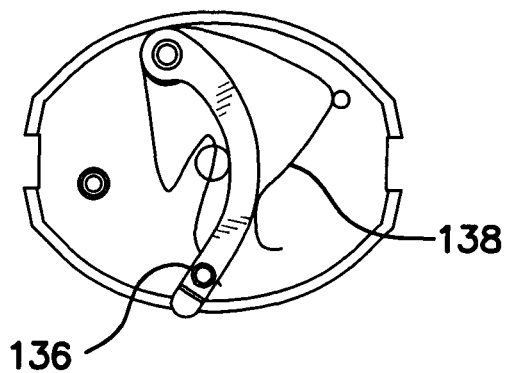
FIGS. 14a-14c depict top views of an obturator in accordance with various aspects of the present invention.
Figure 14B:
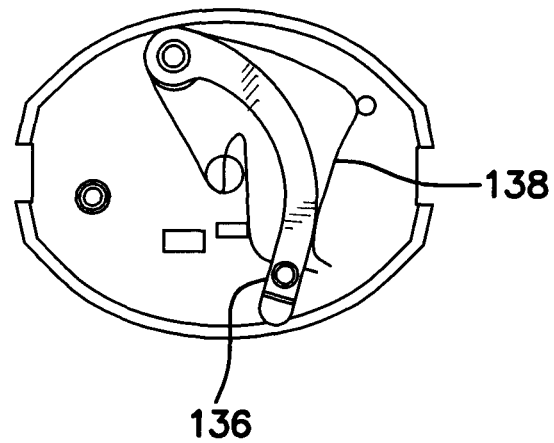
Figure 14C:
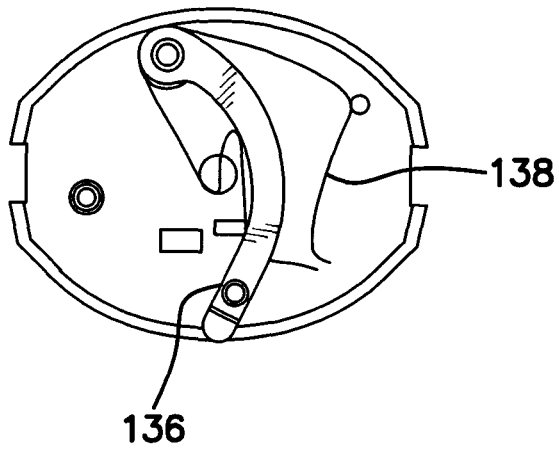

In one aspect, a torsion 126 (FIG. 9), extension 132 (FIG. 12), compression (not shown), or flat spring 134 (FIG. 13) is provided to bias the switch 100 to an initial position. The switch 106 and spring, in one aspect, is combined into one part where the spring is a wire form or single molded configuration that forms the switch, the torsion spring, and the second arm (not shown). In one aspect, the switch 136 is a single piece and the spring 138 (a wire form or single molded piece) incorporates the second arm (FIGS. 14a-14c).

Figure 15A:
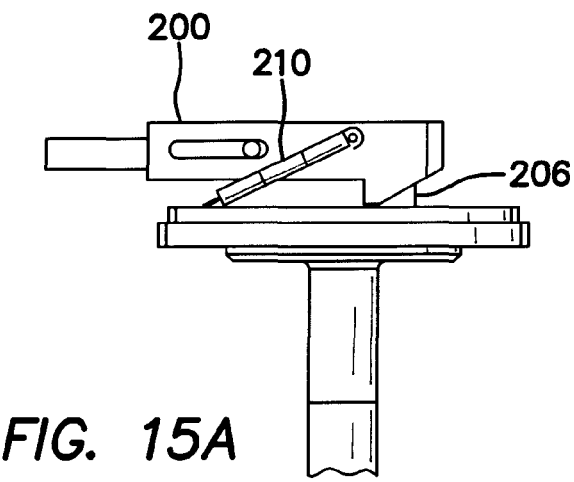
FIGS. 15a-15d depict side views of an obturator in accordance with various aspects of the present invention.
Figure 15B:
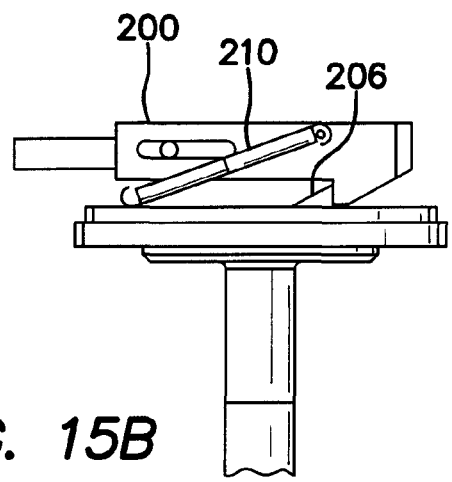
Figure 16A:
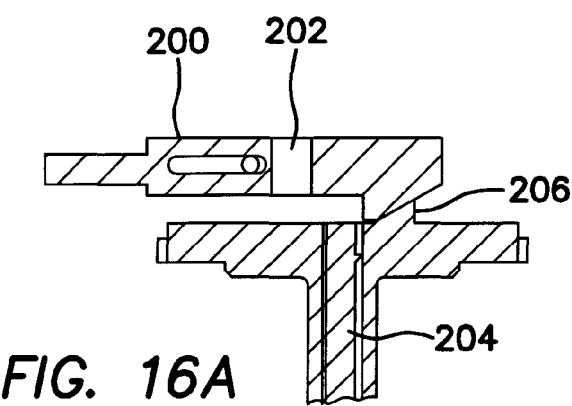
FIGS. 16a-16d depict side views, in cross section, of the obturator of FIGS. 15a-15d.
Figure 16B:
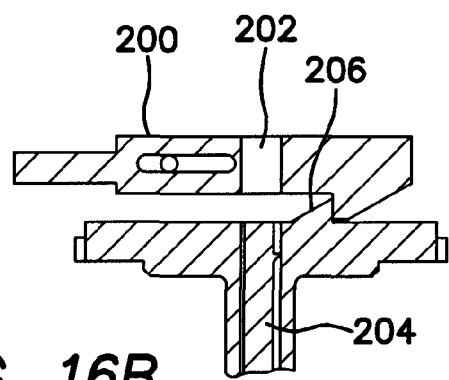
Figure 15C:
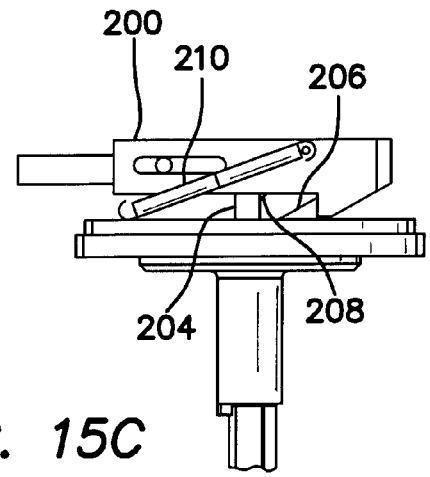
Figure 15D:
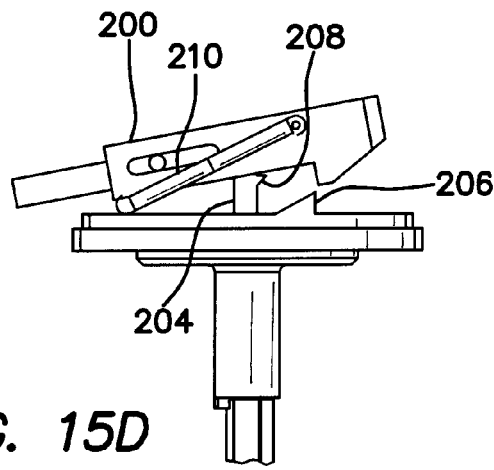
Figure 16C:
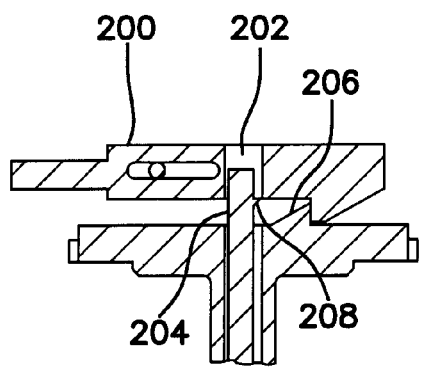
Figure 16D:
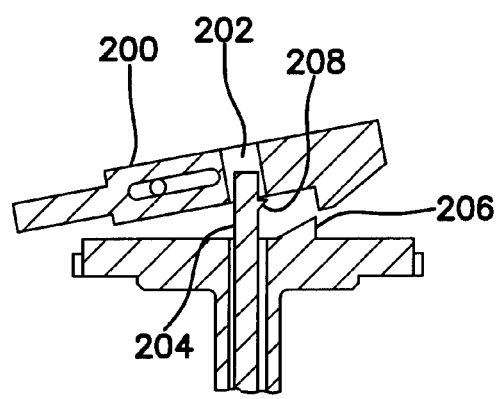
Figure 17:
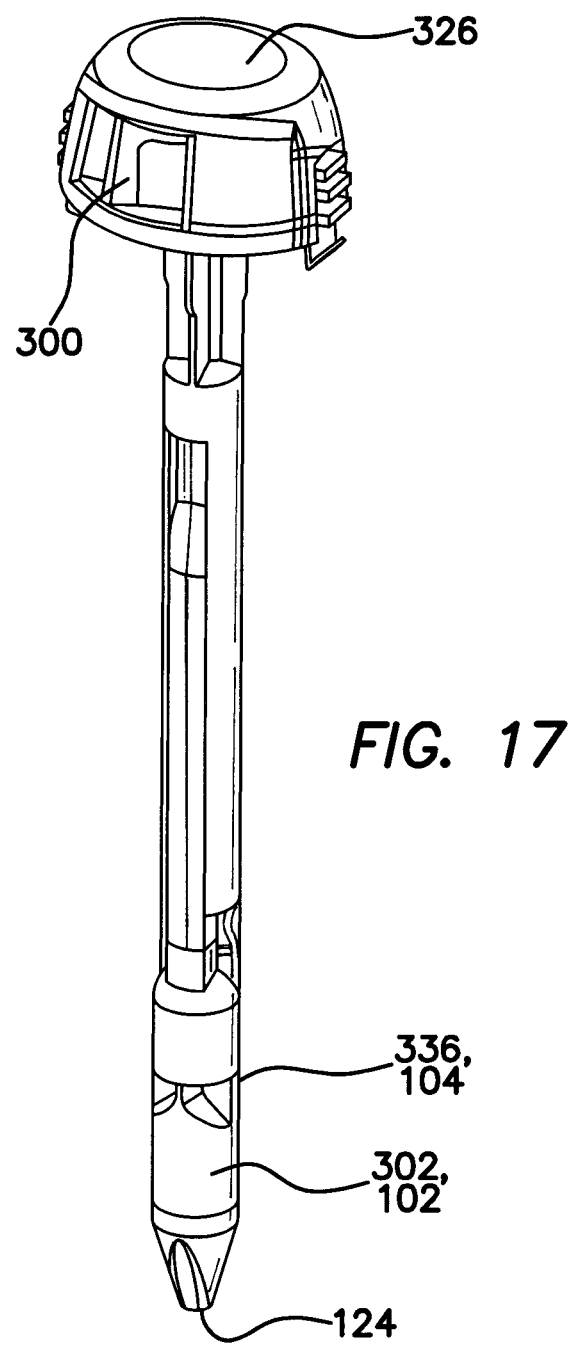
FIG. 17 is a perspective view of an obturator in accordance with various aspects of the present invention.

In FIGS. 15a-15d and 16a-16d, a slide switch 200 is utilized. The switch 200 has a clearance hole 202 in the center for the shield shaft 204. The hole 202 in the switch 200 is offset (FIGS. 15a and 16a), which locks the shield, i.e., preventing retraction of the shield. As the switch 200 is slid to one side (FIGS. 15b and 16b), the switch hooks onto a fixed latch 206, unlocking the shield. The hole 202 in the switch 200 is now aligned with the shield shaft 204 and the shield shaft is free to retract. As the shield shaft 204 retracts, a projection 208, extending from the shield shaft, contacts the switch 200 (FIGS. 15c and 16c). The switch 200 is lifted, which disengages the switch from the fixed latch 206 (FIGS. 15d and 16d). An extension spring 210 pulls the switch 200 to resist disengagement of the switch from the fixed latch 206. As the shield shaft 204 extends back to its original position, the switch 200, under spring force, returns back to its locked position (FIG. 15a).

Figure 18:
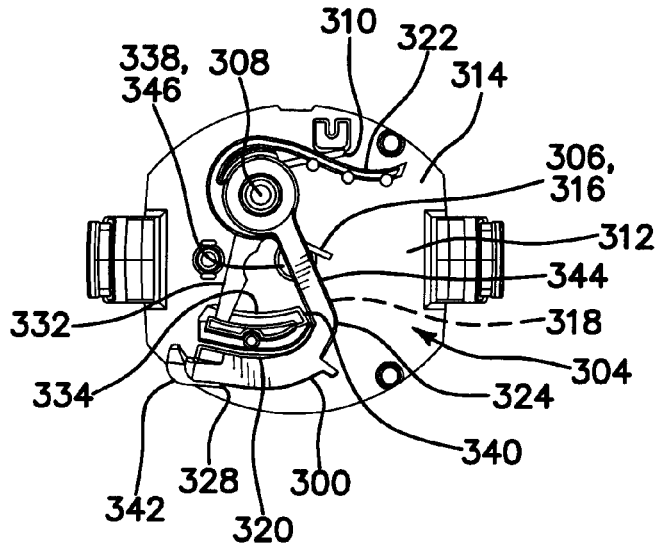
FIG. 18 is a top view of an obturator in accordance with various aspects of the present invention.

Referring to FIGS. 17-22, in one aspect, a multiple piece switch 300 is utilized. As such, after being moved to an unlocked position (FIG. 19), if a portion or component of the switch 300 accessible by a user were interfered or blocked, other portions of the switch continue to operate and thus the shield 302 can be re-locked after use. The switch 300 has a first section, or arm 318, a second section, or arm 332, and a third section, or tab portion 324 having a tab 342 and a tab arm 344. In FIG. 18, the switch 300 is in an initial or resting state. A torsion spring 306 is assembled on the same pivotal post 308 as the switch 300. Switch 300 is rotatable about a longitudinal axis offset from and parallel to the longitudinal axis of the shaft 338. A first leg 310 of the torsion spring 306 will rest against the base plate 312 along the flat surface 314 to the upper right of the post 308 in FIG. 18. A second leg 316 of the torsion spring 306 will rest against the first arm 318 (FIG. 19) of the switch to keep the tab portion 324 pressed against the wall 320 when in this state. The wall 320 is exposed when the tab portion 324 of the switch is moved to the second position. A spring, such as a leaf spring 322, coupled to the tab portion 324 of the switch 300, is not pre-loaded, but rests along the female portion of the boss pin (not shown) attached to the cover 326. The leaf spring 322 may be formed integrally with the tab portion 324 to facilitate manufacturability and assembly of the switch 300.

Figure 19:
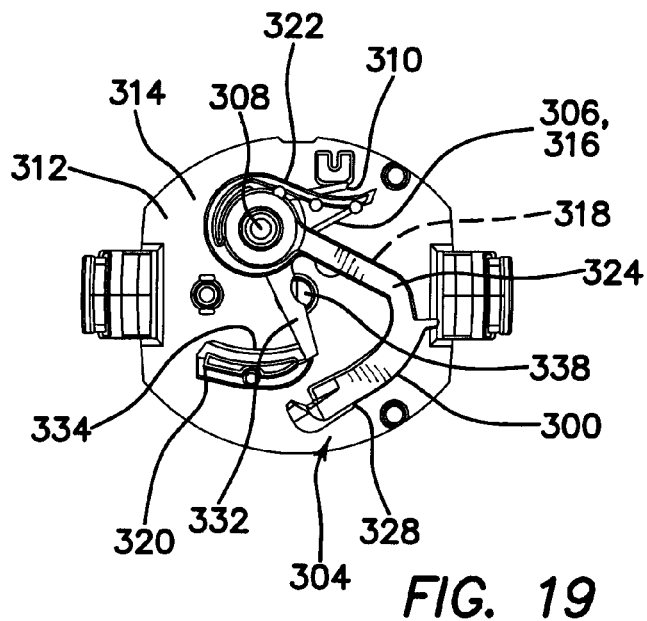
FIG. 19 is a top view of an obturator in accordance with various aspects of the present invention.
Figure 20A:
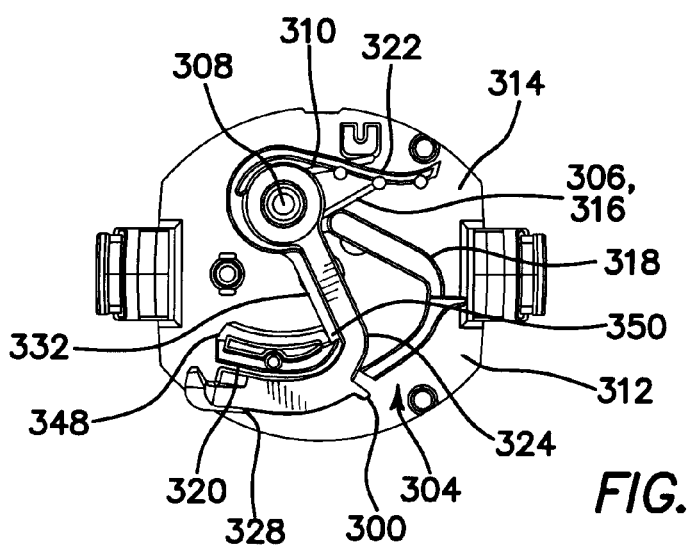
FIG. 20a is a top view of an obturator in accordance with various aspects of the present invention.
Figure 20B:
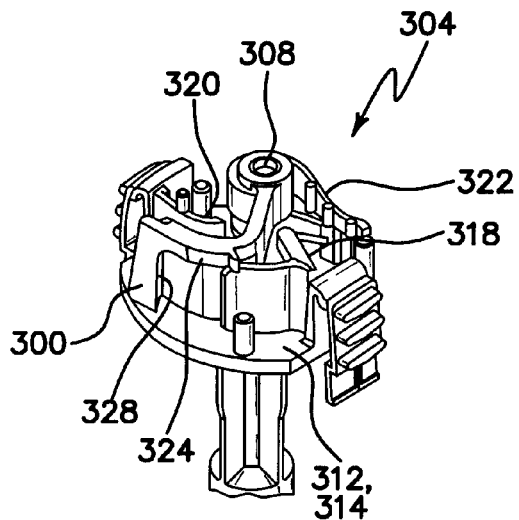
FIGS. 20b-20d depict perspective views of a proximal portion of an obturator in accordance with various aspects of the present invention.
Figure 20C:
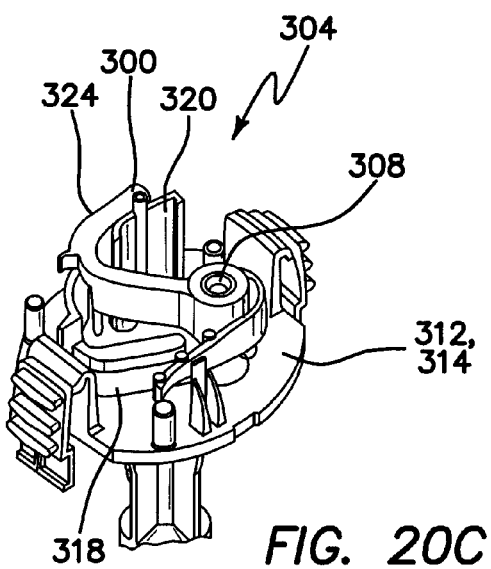
Figure 20D:
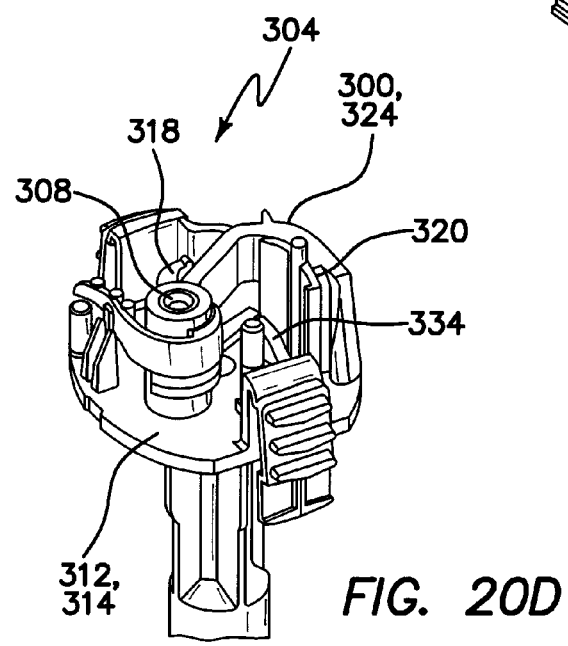
Figure 21A:
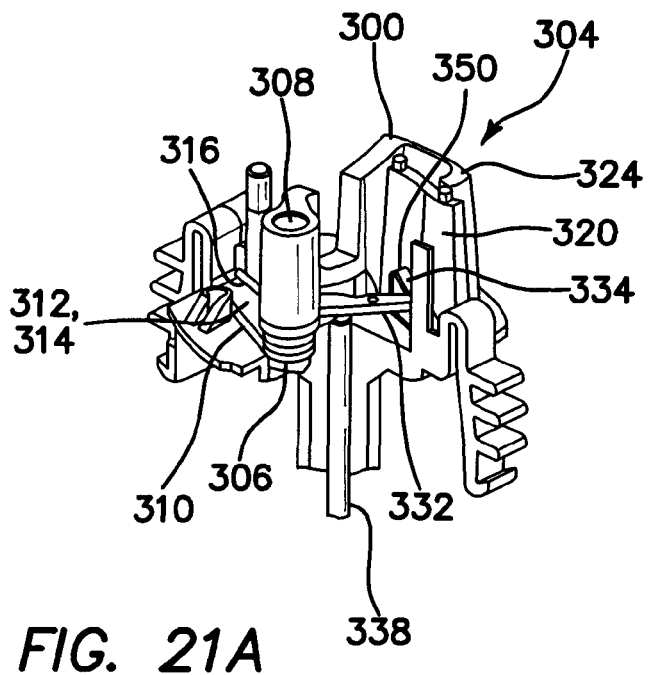
FIGS. 21a-21f depict perspective views of a proximal portion of an obturator in accordance with various aspects of the present invention.
Figure 21B:
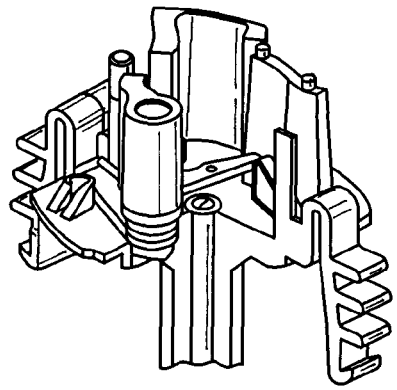
Figure 21C:
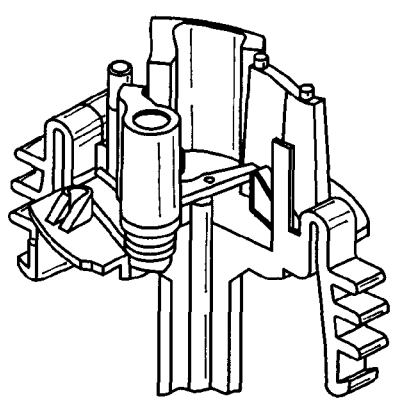
Figure 21D:
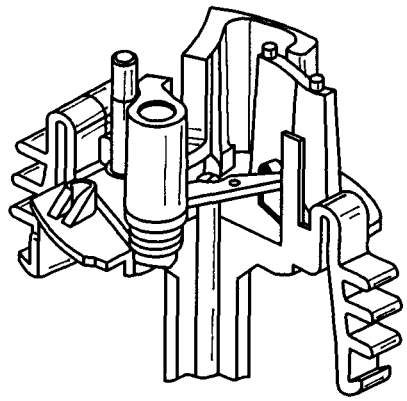
Figure 21E:
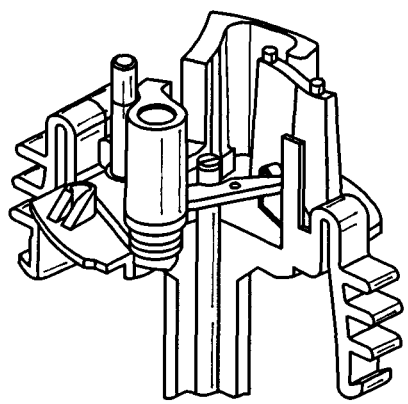
Figure 21F:
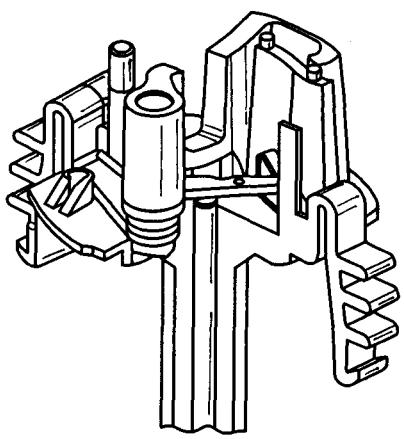

In FIG. 19, as the user slides the tab 342 to rotate the switch 300 to unlock the blade shield 302 (FIG. 17), the tab presses against the first arm 318 of the switch at the flat interface 328, such that the tab, first arm 318 and second arm 332 of the switch rotate together. This causes the thin second arm 332 of the switch 300 to move or deflect up the ramp 334 and hook the back side 340 of the ramp. The second arm 332 is movable or deflectable along a direction parallel to the longitudinal axis of the shaft 338, while the first arm 318 is not deflectable. More particularly, the ramp 334 has a first, low profile end 348 and a second, high profile end 350. The second arm 332 of the switch 300 is adapted to ride along the ramp 334 while deflecting and to snap into a locked position along the back side 340 of the ramp, which is juxtaposed to the high profile end of the ramp, thereby locking the switch into the second position. The ramp 334 obstructs movement of the switch 300 in the second position and allows movement of the switch in the first position. The leaf spring 322 on the tab portion 324 of the switch 300 is now compressed and deformed against the cover boss pin. This causes a small moment on the tab portion 324 in the clockwise direction.

Once the user ceases to apply a load to the switch 300 (i.e., removes his or her finger from the tab 342), the tab portion 324 will automatically return to a nearly closed position (FIG. 20a) while the first arm 318 remains in the second position. In this state, the locking mechanism is disabled or unlocked. The blade shield 302 is free to move, allowing the blade 336 to cut. As the blade shield 302 retracts far enough to expose the blade 336 for cutting, the proximal end 346 of the shaft 338 forces the second arm 332 of the switch 300 over the ramp 334. The torsion spring 306 will force the first arm 318 and second arm 332 of the switch 300 clockwise, back into the locked position against the proximal end 346 of the shield shaft 338 until the compression spring 130 pushes the shield 302 toward covering the blade 336, in which the second arm 332 of the switch 300 resets back to its original, locked position (FIG. 18). Meanwhile, the tap portion 324 remains stationary in this nearly closed position to prevent the user from interfering with the locking mechanism.

Accordingly, the present invention provides a bladed shielded obturator. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

The invention claimed is:

1. An obturator comprising:
   a handle having a switch movable from a first, locked position to a second, unlocked position, the switch having a first section and a second section; and
   a shaft connected to the handle and having a longitudinal axis, the shaft having a movable portion and a fixed portion with a blade connected to the fixed portion of the shaft;
   wherein the first and second section are rotatable with respect to the handle about a second longitudinal axis offset from and parallel to the longitudinal axis of the shaft and the switch in the first position having the first section of the switch obstructing the movable portion of the shaft to prevent movement of the movable portion of the shaft along the longitudinal axis and in the second position having the second section of the switch obstructing the movable portion of the shaft and allowing movement of the movable portion of the shaft along the longitudinal axis; and
   wherein the first section is a first arm coupled to a user accessible tab and the second section is a good arm smaller than the first arm.

2. The obturator of claim 1, wherein the second arm is deflectable in a direction parallel to the longitudinal axis of the shaft.

3. The obturator of claim 2, further comprising a ramp obstructing movement of the switch in the second position and allowing movement of the switch in the first position.

4. The obturator of claim 3, wherein the ramp has a first, low profile end and a second, high profile end, the second section of the switch being adapted to ride along the ramp while deflecting and to snap into a locked position along a back wall of the ramp, juxtaposed to the high profile end of the ramp, thereby locking the switch into the second position.

5. The obturator of claim 1, wherein the first arm is not deflectable.

6. The obturator of claim 1, wherein the user accessible tab and first section are movable to the second position with the user accessible tab returning to the first position while the first section remains in the second position.

7. The obturator of claim 1, further comprising a wall within the handle and being exposed when the switch is moved to the second position.

8. The obturator of claim 1, wherein the second section is movable along a direction parallel to the longitudinal axis.

9. The obturator of claim 1, wherein the first section is not movable along a direction parallel to the longitudinal axis.

10. The obturator of claim 1, wherein the second section is more resilient than the first section.

11. The obturator of claim 1, wherein handle further comprises a pivotal post and wherein the first section and the second section are assembled on the pivotal post.

12. The obturator of claim 11, further comprising a torsion spring assembled on the pivotal post.

13. The obturator of claim 11, wherein the user accessible tab is assembled on the pivotal post.

14. The obturator of claim 1, wherein the user accessible tab comprises a leaf spring coupled thereto.

* * * * *

UNITED STATES PATENT AND TRADEMARK OFFICE
CERTIFICATE OF CORRECTION

| | |
|---|---|
| PATENT NO. | : 8,657,843 B2 |
| APPLICATION NO. | : 12/106227 |
| DATED | : February 25, 2014 |
| INVENTOR(S) | : Andrew N. Hoan et al. |

Page 1 of 1

It is certified that error appears in the above-identified patent and that said Letters Patent is hereby corrected as shown below:

In the Claims

Column 6, line 19: Please change "shaft and the switch" to --shaft, and the switch--.

Column 6, line 57: Please change "wherein handle further" to --wherein the handle further--.

Signed and Sealed this
Twenty-first Day of July, 2015

Michelle K. Lee
*Director of the United States Patent and Trademark Office*